(12) United States Patent
Saint Vil

(10) Patent No.: US 11,921,356 B2
(45) Date of Patent: Mar. 5, 2024

(54) CONTACT LENS CLEANER

(71) Applicant: SainTech, LLC, Richmond, VA (US)

(72) Inventor: Samuel Saint Vil, Glen Allen, VA (US)

(73) Assignee: SainTech, LLC, Richmond, VA (US)

( * ) Notice: Subject to any disclaimer, the term of this patent is extended or adjusted under 35 U.S.C. 154(b) by 837 days.

(21) Appl. No.: 16/743,018

(22) Filed: Jan. 15, 2020

(65) Prior Publication Data
US 2021/0215954 A1 Jul. 15, 2021

(51) Int. Cl.
*G02C 13/00* (2006.01)
*A61L 12/06* (2006.01)

(52) U.S. Cl.
CPC .......... *G02C 13/008* (2013.01); *A61L 12/063* (2013.01); *A61L 2202/121* (2013.01); *A61L 2202/122* (2013.01); *A61L 2202/15* (2013.01); *A61L 2202/182* (2013.01); *A61L 2209/14* (2013.01)

(58) Field of Classification Search
CPC ................ G02C 13/008; A61L 12/063; A61L 2202/121; A61L 2202/122; A61L 2202/15; A61L 2202/182; A61L 2209/14; A61L 12/08; A61L 12/086
See application file for complete search history.

(56) References Cited

U.S. PATENT DOCUMENTS

| | | | |
|---|---|---|---|
| 4,504,994 A | 3/1985 | Johnston | |
| 5,144,144 A | 9/1992 | Borovsky | |
| 5,184,633 A * | 2/1993 | Langford | G02C 13/008 134/102.1 |
| 6,080,361 A * | 6/2000 | Borovsky | A61L 12/086 422/1 |
| 2008/0185024 A1* | 8/2008 | Webb | G02C 13/008 134/84 |
| 2021/0153617 A1* | 5/2021 | Doniga | B08B 3/044 |

OTHER PUBLICATIONS

International Search Report and Written Opinion received for International Application No. PCT/US20/13592 dated Apr. 6, 2020, 10 pages.

* cited by examiner

*Primary Examiner* — Sean E Conley
*Assistant Examiner* — Brendan A Hensel
(74) *Attorney, Agent, or Firm* — Bernard G. Pike; Pike IP law,

(57) ABSTRACT

A contact lens cleaner device which can be used to clean contact lenses from debris and bacteria. The contact lens cleaner device pumps contact lens solution into reservoirs where contact lenses can be placed. The contact lenses rotate within the reservoirs and debris falls into a filter, as the contact lens solution continues to be pumped through the device. UV-lighting kills bacteria and cleanses the contact lenses in the reservoirs.

22 Claims, 2 Drawing Sheets

CONTACT LENS CLEANER

RELATED APPLICATIONS

This patent application claims priority status under 35 U.S.C. § 119(a) to provisional patent application No. 62/792,446 with a filing date of Jan. 15, 2019.

FIELD OF THE INVENTION

A contact lens cleaner device may be used to clean contact lenses with the flow of contact lens solution, a filter system, and UV-lighting.

BACKGROUND OF THE INVENTION

Contact lenses, which are used to enhance eyesight, are generally stored in generic contact lens cases. These cases allow for the contact lenses to rest in a static body of contact lens solution. The contact lens solution is used to retain the moisture of the contact lenses when they are not in use. Generic contact lens cases, however, do not sufficiently clean contact lenses from debris or other harmful material. Contact lenses that are not properly cleaned can cause eye infections, which has led to the rise in popularity of daily contact lenses, instead of long-term contact lenses which stand the risk of being contaminated or lost. There exists a need for a device which can properly clean contact lenses of debris and other harmful materials, like bacteria.

SUMMARY OF THE INVENTION

Embodiments of the contact lens cleaner device for cleaning contact lenses comprise a pump to provide a flow of contact lens solution through a contact lens compartment to physically remove debris from the contact lens. The contact lens solution is pumped through the contact lens compartment housing to at least one contact lens. The pump for circulating contact lens solution through a contact lens storage compartment flushes debris from the lens into a filter or screen to collect the debris and prevent recontamination of the lens. The device may comprise a source of ultraviolet light to provide sterilize the contact lens solution, the contact lens storage compartment, and/or the contact lens. Typically, UV-C radiation is used to kill microbes.

The contact lens cleaner device comprises a left contact lens storage compartment, the left contact lens storage compartment comprising a left reservoir for storing at least one contact lens. The left storage compartment may comprise a left compartment inlet and a left compartment outlet to the reservoir of the contact lens storage compartment. The compartment inlet and the compartment outlet allow the pump to move contact lens solution to flow through the compartment and the reservoir over the contact lens and into the compartment outlet. The debris that is removed from the contact lens, the contact lens compartment and/or the reservoir is moved toward the outlet and into a filter or screen. The device comprises the same previously described components on the right side of the device.

As used herein, contact lens solution means any fluid used to store or clean contact lens such as but not limited to cleaning solutions, rinsing solutions, disinfecting solutions, multipurpose solutions, saline solutions, water, enzymatic cleaning solutions, saltwater, protein remover solution, hydrogen peroxide solutions, or combinations thereof, for example.

The pump comprises a discharge port and a suction port. Embodiments of the contact lens cleaning device may comprise one or more contact lens solution pumps. For example, one pump may pump contact lens solution through both the left storage compartment and the right storage compartment in parallel or series or a separate pump may pump contact lens solution to each of the left storage compartment and the right storage compartment and, therefore, the contact lens cleaning device may comprise two pumps. The discharge port may be in fluid communication with both the left compartment inlet and the right compartment inlet to provide parallel flow through the left compartment and the right compartment. In an alternative embodiment, the pump discharge may be in fluid communication with only one of the left compartment inlet and the right compartment inlet. In such an alternative embodiment, the outlet of the one of the left compartment or the right compartment may flow into the inlet of the other of the left compartment and the right compartment to provide flow in series between the compartments.

The pump may be connected to the compartments or reservoirs with tubing or the compartments or reservoirs may drain or otherwise flow to a sump from which the pump may recirculate the contact lens solution to the compartment or reservoirs.

The contact lens cleaner device may further comprise at least one filter to collect the debris flushed from the contact lens, the compartment, and/or the reservoir(s). In the embodiment of the cleaning device incorporating parallel flow through the left compartment and the right compartment, the contact lens cleaning device may comprise a filter at the exit of both the left compartment and the right compartment or in the suction line of the pump after the outlet of the two compartments are recombined to having a filter inlet and a filter outlet, wherein the filter inlet is in fluid communication with one or both of the first compartment outlet and the second compartment outlet and the filter outlet is in fluid communication with the suction port.

The terminology used herein is for the purpose of describing embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

The embodiments of the described contact lens cleaner device and methods are not limited to the particular embodiments, components, method steps, and materials disclosed herein as such components, process steps, and materials may vary. Moreover, the terminology employed herein is used for the purpose of describing exemplary embodiments only and the terminology is not intended to be limiting since the scope of the various embodiments of the present invention will be limited only by the appended claims and equivalents thereof.

Therefore, while embodiments of the invention are described with reference to exemplary embodiments, those skilled in the art will understand that variations and modifications can be affected within the scope of the invention as defined in the appended claims. Accordingly, the scope of the various embodiments of the present invention should not be limited to the above discussed embodiments and should only be defined by the following claims and all equivalents.

DETAILED DESCRIPTION

Figure 1:
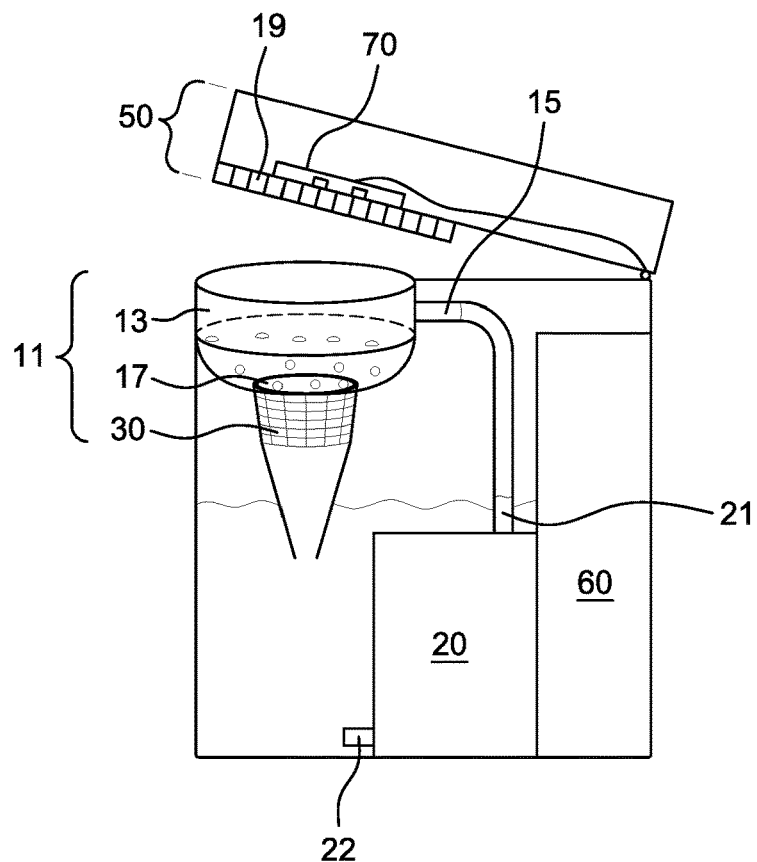
FIG. 1 shows the preferred embodiment of the invention when viewed from the right side with the hingedly connected lid being open. The outer shell of the device is not shown in this figure, to allow for the viewing of the internal components of the invention. Because this view of the invention is from the right side, it does not show those components which are duplicated on the left side.
Figure 2:
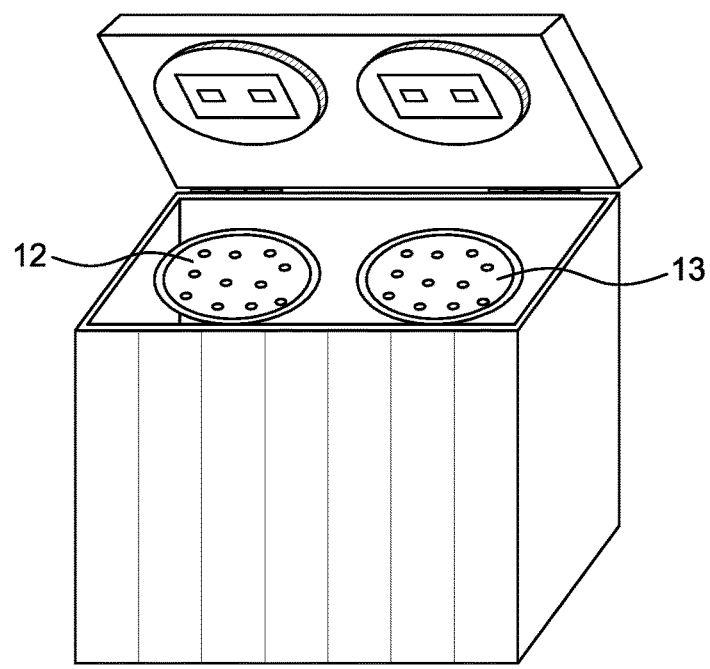
FIG. 2 shows the preferred embodiment of the invention when view from the outside with the hingedly connected lid being open. This view does not show the internal components of the invention.

The preferred embodiment of the contact lens cleaner device, shown in FIG. 1, uses contact lens solution to clean and store contact lenses. As used herein, contact lens solution means any fluid used to store or clean contact lens such as but not limited to cleaning solutions, rinsing solutions, disinfecting solutions, multipurpose solutions, saline solutions, water, enzymatic cleaning solutions, saltwater, protein remover solution, hydrogen peroxide solutions, or combinations thereof, for example. This embodiment comprises a contact lens storage compartment 11, a pump 20, a power supply 60, and a hingedly connected lid 50. The contact lens storage compartment 11 comprises two reservoirs, a right reservoir 13, and a left reservoir 12; two compartment inlets, a right compartment inlet 15, and a left compartment inlet 14; and two compartment outlets, a right compartment outlet 17, and a left compartment outlet 16; and two filters 30. The reservoirs 13 and 12 can each be used to hold a contact lens. In this embodiment, the reservoirs 13 and 12 are concave with a bowl shape. The reservoirs 13 and 12 also comprise a plurality of protrusions. These protrusions can be small holes or nubs that come in contact with the contact lenses, to remove debris from the contact lenses via abrasion. Each reservoir 13 and 12 also comprise an inlet that is tangentially oriented to the circular cross-section of the reservoir. These inlets are the right compartment inlet 15 and the left compartment inlet 14. The compartment inlets 15 and 14 can allow contact lens solution to pour into the reservoirs 13 and 12. The compartment inlets 15 and 14 being tangentially oriented to the circular cross section allow for the flow of contact lens solution to move/rotate the contact lenses. This movement/rotation of the contact lenses, coupled with the plurality of protrusions, enhances the contact lens cleaner device's ability to remove debris from the contact lens. Each reservoir 13 and 12 also comprise a compartment outlet, the right compartment outlet 17, and the left compartment outlet 16. The compartment outlets 17 and 16 are located at the bottom of the reservoirs 13 and 12, and allow contact lens solution to flow out of the reservoirs 13 and 12. The compartment outlets 17 and 16 are each connected to a filter 30. The filters 30 are used to filter debris that has been cleaned from the contact lenses away from the contact lens solution. The filters 30 in this embodiment are a basket-style filters which catch the debris in the filter and allow the contact solution to move through the contact lens cleaner device.

The preferred embodiment in FIG. 1 shows the pump 20. The pump 20 comprises a pump suction port 22 and a pump discharge port 21. The pump suction port 22 sucks in the contact lens solution in the device, as well as the contact lens solution that has passed through the filters 30. The pump discharge port 21 pumps the contact lens solution to the compartment inlets 15 and 14. The power supply 60 is connected to the pump 20, giving it power to perform the work of sucking in the contact solution and pumping it out to the compartment inlets 15 and 14.

In this embodiment in FIG. 1, the hingedly connected lid 50 is located on the top of the contact lens cleaner device, and comprises two contact lens storage compartment lids 19, and two UV-lights 70. In this embodiment, the UV-lights 70 are comprise of UV-C lights. The contact lens storage compartment lids 19 partially or fully cover each of the reservoirs 13 and 12. The contact lens storage compartment lids 19 are able to protect the contact lenses from any debris outside of the device, and also secure the contact lenses if the contact lens cleaner device is moved or transported. The contact lens storage compartment lids 19 also keep the contact lens solution from leaking from the device. The UV-lights 70 are located above each of the reservoir 13 and 12. In this embodiment the UV-lights 70 are built into the contact lens storage compartment lids 19. The UV-lights 70 are able to clean the contact lens solution with the light and kill bacteria on the contact lenses with the light. The UV-lights 70 are connected to the power supply 60.

Figure 3:
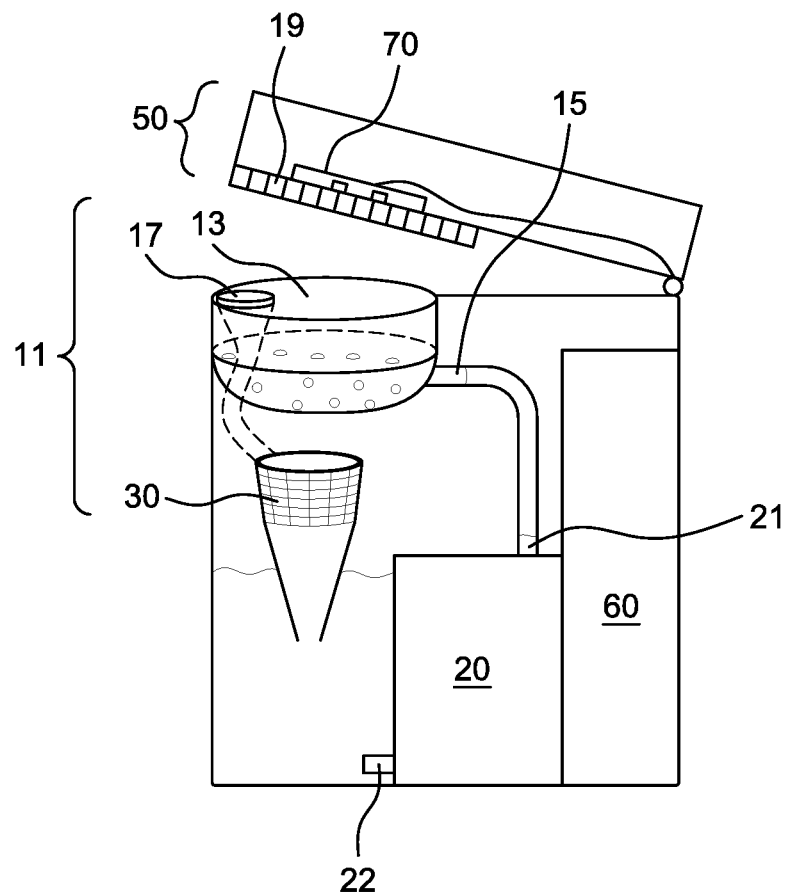
FIG. 3 shows an additional embodiment of the invention when viewed from the right side with the hingedly connected lid being open. The outer shell of the device is not shown in this figure, to allow for the viewing of the internal components of the invention. Because this view of the invention is from the right side, it does not show those components which are duplicated on the left side.

An additional embodiment of the contact lens cleaner device 10 is shown in FIG. 3. In this embodiment, the compartment outlets 17 and 16 are located near top of the reservoirs 13 and 12 and above the compartment inlets 15 and 14, instead of at the bottom of the reservoirs 13 and 12. The compartments outlets 17 and 16 being located higher allows them to act like an overflow, similar to how an overflow works in a residential sink. In this embodiment, contact solution would still be pumped via the pump 20, and flow through the compartment inlets 15 and 14, into the reservoirs 13 and 12, but as the reservoirs 13 and 12 became filled the contact lens solution would flow into the compartment outlets 17 and 16. The compartment outlets 17 and 16 would also allow the flow of debris into the filters 30.

Additional embodiments of the contact lens cleaner device, comprise different types of filters 30. The filters 30 could be of another style than a basket-style filter; they could also be screens. In another embodiment, the invention may comprise only one filter that allows the flow of contact lens solution coming from both compartment outlets 17 and 16. In another embodiment, the invention may comprise one pump 20, that pumps the contact lens solution in a series, or in parallel, or in another pattern; the invention can also comprise more than one pump: one for pumping solution to each compartment inlet 15 and 14. Another embodiment of the invention could comprise a system of compartment inlets and outlets which are utilized by both reservoirs 13 and 12, where one there is one compartment inlet that allows the flow of contact lens solution into both reservoirs 13 and 12, and one compartment outlet also shared by both reservoirs 13 and 12. In another embodiment of the invention the power supply 60 could be a battery, multiple batteries, or another similar form of power supply. In another embodiment of the invention, there may be only one contact lens storage lids 19 that covers both reservoirs 13 and 12, or the contact lens storage compartment lids 19 could cover the reservoirs 13 and 12 by screwing on or snapping in place. In another embodiment of the invention, one UV-light, or a plurality of UV-lights may be used in place of two UV-lights 70. In another embodiment of the device, the contact lens storage compartment 11 may be detachable from the rest of the device, allowing for cleaning or replacement. In another embodiment of the device, a pump controller may be used to control the pump 20. This controller may be in the form of a button on the device, or some other form of controller.

The invention claimed is:

1. A contact lens cleaner device, comprising:
a contact lens storage compartment, the contact lens storage compartment comprising:
a reservoir for storing at least one contact lens wherein the reservoir is a bowl-shaped compartment for receiving a contact lens having a concave inner surface and the concave inner surface has a plurality of protrusions on top of which the contact lens is received to remove debris from the contact lenses via abrasion, and the plurality of protrusions being distributed throughout the surface area of the concave inner surface to form an abrasive surface;
an inlet to the reservoir of the contact lens storage compartment;
an outlet from the reservoir of the contact lens storage compartment;
a pump comprising a discharge port and a suction port, wherein the discharge port is in fluid communication with the inlet to the contact lens storage compartment and
a filter having a filter inlet and a filter outlet, wherein the filter inlet is in fluid communication with the outlet from the contact lens storage compartment and the filter outlet is in fluid communication with the suction port.

2. The contact lens cleaner device of claim 1, wherein the reservoir has a circular cross-section and the inlet is oriented tangentially to the circular cross-section.

3. The contact lens cleaner device of claim 1, wherein the plurality of protrusions are small nubs.

4. The contact lens cleaner device of claim 1, wherein the filter is a screen in the outlet of the reservoir.

5. The contact lens cleaner device of claim 1, comprising a pump controller, wherein the pump controller controls a pumping cycle for the pump.

6. The contact lens cleaner device of claim 5, comprising a battery as the power source.

7. The contact lens cleaning device of claim 1, comprising a source of ultraviolet light to irradiate the reservoir.

8. The contact lens cleaning device of claim 7, wherein the source of ultraviolet light is a source of UV-C light.

9. The contact lens cleaning device of claim 1, wherein the compartment outlet is in a top portion of the inner surface of the reservoir.

10. The contact lens cleaning device of claim 3, comprising a removable lid to cover the reservoir.

11. The contact lens cleaning device of claim 1, wherein the contact lens compartment is detachable from the device.

12. A contact lens cleaning device, comprising:
a left contact lens storage compartment, the left contact lens storage compartment comprising a left reservoir for storing a left contact lens, wherein the left reservoir is a bowl-shaped compartment for receiving a contact lens having a left concave inner surface and the left concave inner surface has a plurality of protrusions on top of which the contact lens is received to remove debris from the left contact lens via abrasion, and the plurality of protrusions being distributed throughout the surface area of the left concave inner surface to form an abrasive surface;
a left compartment inlet to the left reservoir of the left contact lens storage compartment;
a left compartment outlet from the left reservoir of the contact lens storage compartment; and
a filter, the filter having a filter inlet and a filter outlet;
a right contact lens storage compartment, the right contact lens storage compartment comprising:
a right reservoir for storing a right contact lens, wherein the right reservoir is a bowl-shaped compartment for receiving a right contact lens having a right concave inner surface and the right concave inner surface has a plurality of protrusions on top of which the contact lens is received to remove debris from the right contact lens via abrasion, and the plurality of protrusions being distributed throughout the surface area of the right concave inner surface to form an abrasive surface;
a right compartment inlet to the right reservoir of the right contact lens storage compartment;
a right compartment outlet from the right reservoir of the contact lens storage compartment; and
a pump comprising a discharge port and a suction port, wherein the discharge port is in fluid communication with both the left compartment inlet and the right compartment inlet.

13. The contact lens cleaning device of claim 12, wherein the right and left contact lens compartments are detachable from the device.

14. The contact lens cleaning device of claim 12, wherein the filter inlet is in fluid communication with one or both of the right compartment outlet and the left compartment outlet and the filter outlet is in fluid communication with the suction port.

15. The contact lens cleaner device of claim 12, wherein the reservoir has a circular cross-section and the inlet is oriented tangentially to the circular cross-section.

16. The contact lens cleaner device of claim 12, wherein the filter is a screen in the outlet of the reservoir.

17. The contact lens cleaner device of claim 12, comprising a pump controller, wherein the pump controller controls a pumping cycle for the pump.

18. The contact lens cleaner device of claim 17, comprising a battery as the power source.

19. The contact lens cleaning device of claim 12, comprising a source of ultraviolet light to irradiate the reservoir.

20. The contact lens cleaning device of claim 19, wherein the source of ultraviolet light is a source of UV-C light.

21. The contact lens cleaning device of claim 12, wherein the right compartment outlet is in a top portion of the right concave inner surface of the right reservoir and the left compartment outlet is in a top portion of the left concave inner surface of the left reservoir.

22. The contact lens cleaning device of claim 12, comprising a removable lid to cover the left reservoir and the right reservoir.

\* \* \* \* \*